US00PP15761P2

(12) United States Plant Patent
Kawashima

(10) Patent No.: US PP15,761 P2
(45) Date of Patent: May 10, 2005

(54) ***OSTEOSPERMUM* PLANT NAMED 'KAKEGAWA AU10'**

(50) Latin Name: *Osteospermum×fruticosum*
Varietal Denomination: Kakegawa AU10

(75) Inventor: Moriya Kawashima, Matsumoto (JP)

(73) Assignee: Sakata Seeds Corporation, Yokohama (JP)

( * ) Notice: Subject to any disclaimer, the term of this patent is extended or adjusted under 35 U.S.C. 154(b) by 37 days.

(21) Appl. No.: 10/775,617

(22) Filed: Feb. 10, 2004

(51) Int. Cl.[7] ..... A01H 5/00
(52) U.S. Cl. ..... Plt./360
(58) Field of Search ..... Plt./360

*Primary Examiner*—Anne Marie Grunberg
*Assistant Examiner*—June Hwu
(74) *Attorney, Agent, or Firm*—Jondle & Associates P.C.

(57) ABSTRACT

An *Osteospermum* cultivar particularly distinguished by its purple-pink flower color and tendency to hold flowers open later in the evening.

1 Drawing Sheet

Genus and species: *Osteospermum fruticosum.*
Variety denomination: 'Kakegawa AU10'.

BACKGROUND OF THE NEW PLANT

The variety 'Kakegawa AU10' originated from a gene pool population made in 1999 in Misato, Japan. In May 1999, three varieties were intercrossed and seed from these three plants were bulked to make the population. The three varieties were 'Brightside' (U.S. Plant Pat. No. 10,596), 'Purple Passion' (unprotected, now only available in 'Passion Mix') and an unnamed breeding line of unknown origin. The unnamed breeding line possessed purple flowers, an erect plant habit and very vigorous growth. It is not known which two varieties were the actual parents for 'Kakegawa AU10'. Seed from this population was sown in April 2000 and plants were transplanted to the outdoor field. In August 2000, selections were made for vegetative propagation using plant habit, ability to bloom during warm temperature periods and flower color as selection criteria. One selection, designated breeder code M1-77, became the new variety 'Kakegawa AU10'. The variety 'Kakegawa AU10' was found to be stable and reproduce true to type in successive generations of asexual propagation.

DESCRIPTION OF PHOTOGRAPHS

This new *Osteospermum* plant is illustrated by the accompanying photographs which show the blooms and foliage of the plant in full color. The colors shown are as true as can be reasonably obtained by conventional photographic procedures.

DESCRIPTION OF THE NEW CULTIVAR

Figure 1:
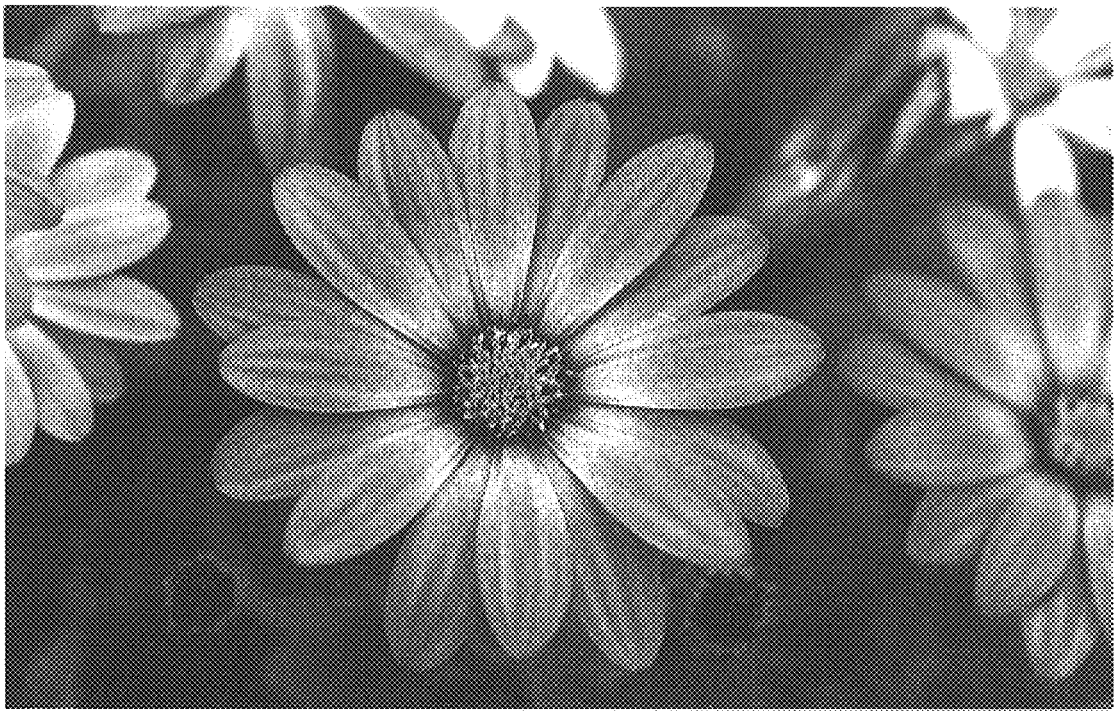
FIG. 1 shows a close-up view of a single inflorescence.
Figure 2:
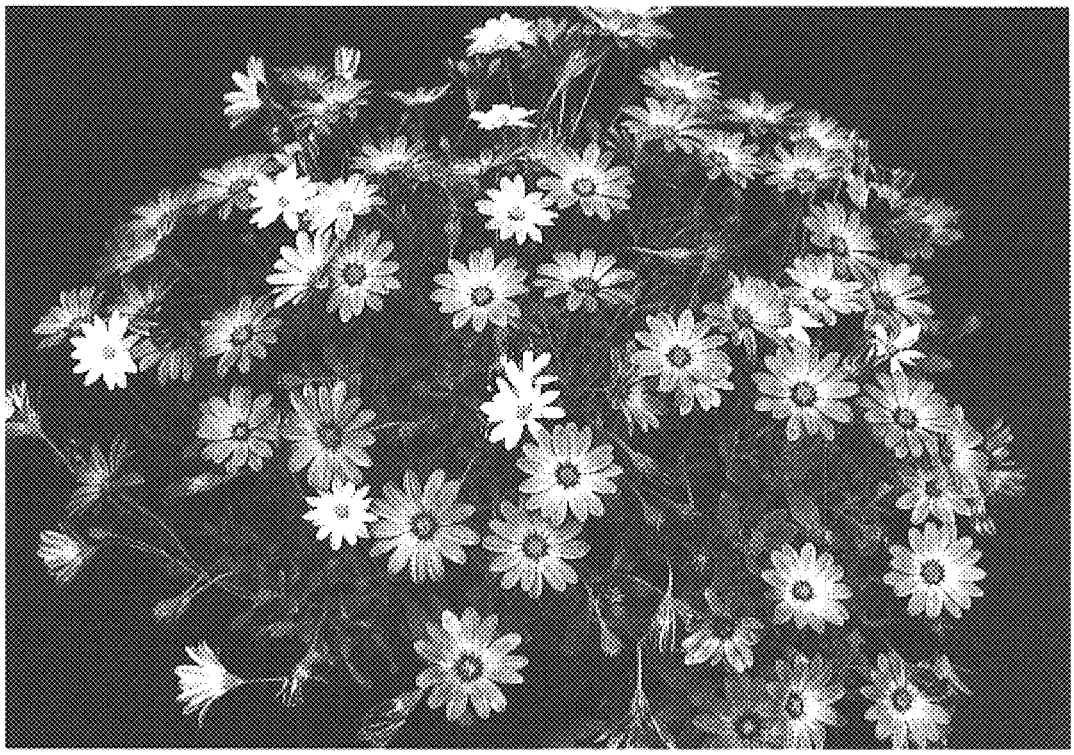
FIG. 2 shows a side view of the entire plant including its flower buds, open blooms and foliage.

The following detailed descriptions set forth the distinctive characteristics of 'Kakegawa AU10'. The data which defines these characteristics were collected from asexual reproductions carried out in Salinas, Calif. Data was collected on plants 28 weeks from tranplanting rooted cuttings into 16 cm diameter pots, one plant per pot. Color references are to The R.H.S. Colour Chart of The Royal Horticultural Society of London (R.H.S).

DESCRIPTION OF THE NEW PLANT

Classification:
*Family.*—Compositae.
*Botanical.*—*Osteospermum fruticosum.*
*Commercial name.*—Cape Daisy.

Parentage: The female and male parents are unknown. This new variety was selected from a gene pool population that was created by intercrossing the varieties 'Brightside' (U.S. Plant Pat. No. 10,596), 'Purple Passion' (unprotected, now only available in 'Passion Mix') and an unnamed breeding line with purple flowers, an erect plant habit and very vigorous growth.

Growth:

*Time to produce a rooted cutting.*—Cuttings will colonize a 2.5 cm diameter by 2.5 cm tall greenhouse tray cell with peat-based plant media in approximately five weeks. Cuttings are dipped in a normal dilution (1:9) of DIP 'N GROW root inducing solution in water. The trays are misted hourly during rooting.

*Environmental conditions for plant growth.*—Rooted cuttings are transplanted to pots with a 16 cm diameter, one plant per pot. Peat moss-based growing media is used. The pots are watered using a 150–200 ppm fertilizer solution containing 18% nitrogen, 8% phosphorus and 18% potassium. The soil is allowed to dry between waterings. During the first few weeks after transplanting the plants should have evening temperatures around 15–18° C. for good root growth. When plants reach 7.5–10 cm in height they are pinched back to 5–6 leaves to promote branching. The plants are grown through the winter in cool greenhouses (10–15° C.) with no shading to keep their habit compact. In spring, after the plants have received at least four weeks of cool conditions to vernalize, warmer temperatures can be used to promote blooming. Spring and summer daytime high temperatures in Salinas, Calif., where the data was collected, range from 16–25° C.

*Time to bloom from propagation.*—18–20 weeks when rooted vegetative cuttings are transferred to a six-inch diameter pot in late fall and given several weeks of below 50 degree Fahrenheit temperature prior to increasingly warmer spring weather. Floweing season is in April through June and is temperature (required to initiate bud development) and day length dependent (long days). They will stop flowering when temperatures are too high, such as in the southern areas of the country.

*Habit.*—Upright and branching.

*Life cycle.*—Perennial.

Plant:

*Form.*—Branching, dense.

*Plant size.*—Height is 45–65 cm; width 60–80 cm.

Stems:

*Anthocyanin color.*—None.

*Internode length.*—0.5–2.0 cm.

*Pubescence.*—Glabrous.

*Pubescence shape.*—Linear.

*Pubescence color.*—White (RHS N155A).

*Stem color.*—Yellow-green (RHS 144A).

*Stem description.*—Strong, erect.

*Stem diameter.*—5.0–6.0 mm.

Leaves:

*Arrangement.*—Alternate.

*Shape.*—Oblanceolate.

*Apex.*—Acute.

*Base.*—Decurrent.

*Margin.*—Serrate.

*Venation.*—Pinnate.

*Surface.*—Dull, rough.

*Surface pubescence.*—Slight, white (RHS N155A).

*Length.*—6.0–7.0 cm.

*Width.*—2.5–3.5 cm.

*Thickness.*—1.0 mm.

*Color.*—Upper is green (RHS 147A); Lower is green (RHS 137A).

*Venation color.*—Upper is yellow-green (RHS 144A); Lower is yellow-green (RHS 144A).

Inflorescence:

*Type.*—Capitulum (head); disc florets are staminate and ray florets are carpellate.

*Diameter.*—5.5–6.0 cm.

*Depth.*—1.0–1.5 cm.

*Petal numbers.*—15–18.

*Disc diameter.*—0.9–1.1 cm.

*Disc floret number.*—60–70.

*Flowering habit.*—Determinate.

*Flowers life span.*—3–4 days.

*Fragrance.*—None.

*Seed production.*—None.

*Peduncle length.*—3.0–5.5 cm.

*Peduncle diameter.*—2.0 mm.

*Peduncle color.*—Yellow-green (RHS 144A).

*Peduncle texture.*—Dull, slight pubescence.

*Phyllaries.*—15–18 per inflorescence, free, arranged symmetrically; Length — 6.0–8.0 cm; Width — 1.0–2.0 mm; Apex — Acute; Margin — Entire; Shape — Linear, acute tip; Color — Upper, green (RHS 143A); Lower, green (RHS 143A).

Ray florets:

*Bud color.*—143A (green) vertically alternating with 144C (yellow-green); initial ray floret color is 151D (yellow-green).

*Bud shape.*—Longitudinal cross-section is obovate.

*Bud surface texture.*—Pubescent.

*Bud apex.*—Mucronate.

*Bud base.*—Truncate.

*Bud size.*—Length is 1.0–1.2 cm; Diameter is 0.6–1.0 cm.

*Corolla.*—One petal per ray floret. Only the outer row of florets are the ray florets.

*Ovary.*—Superior.

*Petals length.*—2.3–2.7 cm.

*Petal width.*—0.8–9.0 cm.

*Petal shape.*—Spatulate.

*Petal apex.*—Obtuse with tiny indentation at tip.

*Petal margin.*—Entire.

*Mature petal color.*—Upper, purple (RHS N78A) fading to white (RHS N155A) near the base. Basal most 3–4 mm purple-violet (RHS 80B); Lower, center stripe 4 mm purple (RHS 78D), 2 outer stripes 2 mm yellow (RHS 3D), Margin stripes 1 mm purple (RHS 82C).

*Immature petal color.*—Upper, white (155A).

*Fading ray florets colors.*—Basal 3–4 mm purple-violet (80B), central portion white (155A) fades quickly to purple (77B) and purple (77C) over the entire floret.

*Petal pubescence.*—Glabrous.

*Pistil form.*—One style with two stigma branches.

*Pistil length.*—3–4 mm.

*Stigma color.*—Violet-blue (RHS 92C).

*Style color.*—White (RHS N155A).

Disc florets:

*Color.*—(Color at top, as seen looking at inflorescence) green (RHS 143A).

*Shape.*—Tubular.

*Apex.*—Rounded.

*Surface.*—Pubescent.

*Size.*—Length 1.0 cm; width 1.0 mm.

*Stamens.*—5, fused into a single tube.

*Anther color.*—Violet-blue (RHS N92C).

*Pollen color.*—Orange (RHS 25B).

DISEASE AND INSECT RESISTANCE

'Kakegawa AU10' is very disease resistant but it can be susceptible to aphids, thrips, whiteflies and worms.

COMPARISON WITH KNOWN CULTIVARS

'Kakegawa AU10' is a distinct variety of *Osteospermum* owing to its petal color and the contrast between white petal base and colored petal center and tip. The new variety is different from the cultivars 'Brightside' and 'Purple Passion' mainly in flower color. 'Brightside' has white flowers and 'Purple Passion' has purple flowers. 'Kakegawa AU10' is most similar to the variety 'Highside', the subject of U.S. Plant Pat. No. 10,595; however, there are numerous differences as shown in Table 1 below.

TABLE 1

| Trait | 'Kakegawa AU10' | 'Highside' |
|---|---|---|
| Upper Petal Colors | Purple-pink petals with shades of purple (RHS N78A) fading to white and then to a lighter purple-pink (RHS 80B) at the petal base | Red-purple (RHS 72B) with shades of lighter red-purple (RHS 70B) between petal veins |
| Inflorescence Diameter | 5.0–6.0 cm | 5.5–7.0 cm |
| Pollen Color | Orange (RHS 25B) | Yellow-orange (RHS 23A) |
| Stem Branching | Stems branch many times without pruning | Stems must be pinched at tip to promote branching |
| Ability to Flower when warm | Will continue to flower even if night time temperatures are above 50 degrees Fahrenheit | Flower bud formation stops if night temperatures do not drop below 50 degrees Fahrenheit |

I claim:

1. A new and distinct cultivar of *Osteospermum* plant, as shown and described herein.

* * * * *